United States Patent
Brown et al.

(10) Patent No.: US 7,056,299 B2
(45) Date of Patent: Jun. 6, 2006

(54) DEVICE FOR HEEL SHOCK ABSORPTION, SWELLING, AND PAIN TREATMENT

(75) Inventors: Ivan E. Brown, Spirit Lake, IA (US); Ronald S. Krivosha, Bellevue, WA (US)

(73) Assignee: Brown Medical Industries, Spirit Lake, IA (US)

( * ) Notice: Subject to any disclaimer, the term of this patent is extended or adjusted under 35 U.S.C. 154(b) by 0 days.

(21) Appl. No.: 10/938,997

(22) Filed: Sep. 10, 2004

(65) Prior Publication Data

US 2006/0058722 A1 Mar. 16, 2006

(51) Int. Cl.
*A61F 13/00* (2006.01)
*A61F 13/06* (2006.01)

(52) U.S. Cl. ............... 602/61; 602/62; 602/65; 602/66; 128/892; 128/893; 128/894

(58) Field of Classification Search ............ 602/23, 602/27, 60–63, 65–66, 75; 128/882, 889, 128/892–894, 888
See application file for complete search history.

(56) References Cited

U.S. PATENT DOCUMENTS

| | | | | |
|---|---|---|---|---|
| 792,688 A | * | 6/1905 | Bliss | 36/37 |
| 1,406,583 A | * | 2/1922 | Ruge | 602/66 |
| 3,322,118 A | * | 5/1967 | Sotherlin | 128/892 |
| 3,648,291 A | * | 3/1972 | Pankers | 2/16 |
| 3,990,440 A | * | 11/1976 | Gaylord, Jr. | 128/892 |
| 4,085,745 A | * | 4/1978 | Alenares | 602/63 |
| 4,137,654 A | * | 2/1979 | Hlavac | 36/117.5 |
| 4,166,460 A | * | 9/1979 | Applegate | 602/27 |
| 4,314,412 A | * | 2/1982 | Anderson et al. | 36/100 |
| 4,476,858 A | * | 10/1984 | Curtis | 602/23 |
| 4,762,123 A | * | 8/1988 | Dedo | 128/898 |
| 4,974,343 A | * | 12/1990 | Davidson | 36/89 |
| 5,052,128 A | * | 10/1991 | Lonardo | 36/11.5 |
| 5,092,347 A | * | 3/1992 | Shaffer et al. | 128/892 |
| 5,645,525 A | * | 7/1997 | Krivosha | 602/62 |
| 5,891,073 A | * | 4/1999 | Deirmendjian et al. | 602/27 |
| 6,001,122 A | * | 12/1999 | Lyles | 607/111 |
| 6,059,744 A | * | 5/2000 | Hardt | 602/62 |
| 6,142,967 A | * | 11/2000 | Couch | 602/66 |
| 6,558,339 B1 | * | 5/2003 | Graham | 602/66 |
| 2001/0047146 A1 | * | 11/2001 | Toda | 602/62 |
| 2002/0032485 A1 | * | 3/2002 | Flam et al. | 623/23.51 |
| 2003/0055368 A1 | * | 3/2003 | Jacoby | 602/27 |

OTHER PUBLICATIONS

MSN Encarta, "fluid", printed Jun. 11, 2005, 2 pages.*

* cited by examiner

*Primary Examiner*—Henry Bennett
*Assistant Examiner*—Amanda Wieker
(74) *Attorney, Agent, or Firm*—McKee, Voorhees & Sease, P.L.C.

(57) ABSTRACT

An orthotic device for absorption of heel shock, treating edema and swelling and for lessening pain. It is comprised of an elastic sleeve adapted to fit over the foot and heel of a person. The sleeve includes a shock absorbing heel pad inside of the sleeve in a position to be disposed under the heel when the sleeve is worn around the heel. The sleeve is of elastomeric material providing compression to treat edema and swelling. The pad may be a polymeric plastisol material which can be cooled to provide cold therapy and positioned under the heel to provide cushioning and shock absorption.

15 Claims, 2 Drawing Sheets ical data, 25 including pages of tables and references.

DEVICE FOR HEEL SHOCK ABSORPTION, SWELLING, AND PAIN TREATMENT

FIELD OF THE INVENTION

The present invention relates generally to an orthotic device that simultaneously provides plantar shock absorption for heel pain, reduced inflammation with optional cold therapy, and also treats edema and swelling with compression.

BACKGROUND OF THE INVENTION

There are prior art devices which are used to treat ankle pain by immobilizing the ankle and the foot. Such devices include tape, elastic wrappings, lace-up braces, or slip-on braces with straps. Other prior art devices include high top shoes with supports and inflatable bladders covering the ankle bones to support the ankle.

Like ankle pain, heel pain is also a relatively common complaint. However, heel pain is medically and anatomically distinguishable from ankle pain rendering prior art ankle braces ineffective in treating heel pain without also affecting the range of motion of the ankle. Therefore, a need can be seen for effective ways to treat heel pain without affecting the range of motion of the ankle.

The ethiology of heel pain includes (1) trauma, such as contusions; (2) bio-mechanical conditions such as Pes Plano Valgus and Equinus; (3) anatomical abnormalities such as heel spurs, narrow heels, and a decreased plantar fat pad; (4) inflammatory problems such as bursitis, tendonitis, plantar fascitis, calcaneoapophysitis; and (5) poorly fitted shoes.

Prior art methods to treat heel pain include ice therapy, limiting weight bearing, heel pads, heel cups, orthotic devices, surgical procedures, immobilization casting, and oral and injected anti-inflammatory medications.

Another device owned by the common Assignee of the present invention U.S. Pat. No. 5,645,525. There is disclosed a heel stabilizing device which takes advantage of an elastic sleeve adapted to fit around the foot with cushioning pads positioned laterally to stabilize the foot. This invention represents a variation of that device, offered specifically for a reduction of plantar shock absorption for heel pain with a device that can be used with or without a shoe.

It is a primary objective of the present invention to provide an elastic sleeve medical (orthotic) device that can simultaneously provide plantar shock absorption for heel pain, reduce inflammation with optional cold therapy, and at the same time treat edema and swelling with compression.

The above primary objective is provided with a device which fits like a stocking and feels comfortable such that it can easily be worn in the environment of using a shoe, for example an athletic shoe if one desires to do so.

The method of accomplishing these as well as other objectives of the invention will become apparent from the detailed description which follows hereinafter.

SUMMARY OF THE INVENTION

An orthotic device for absorption of heel shock, treating edema and swelling and for lessening pain. It is comprised of an elastic sleeve adapted to fit over the foot and heel of a person. The sleeve includes a shock absorbing heel pad inside of the sleeve in a position to be disposed under the heel when the sleeve is worn around the heel. The sleeve is of elastomeric material providing compression to treat edema and swelling. The pad may be a polymeric plastisol material which can be cooled to provide cold therapy and positioned under the heel to provide cushioning and shock absorption.

DETAILED DESCRIPTION OF THE PREFERRED EMBODIMENT

The present invention will be described as it applies to its preferred embodiment. It is not intended that the present invention be limited to the described embodiment. It is intended that the invention cover all alternatives, modifications, and equivalences which may be included within the spirit and scope of the invention. It may be used in conjunction with the invention of U.S. Pat. No. 5,645,525, issued Jul. 8, 1997 if one wishes, wherein a pair of pads are disposed in the opposite sides of the inside surface of the sleeve and opposite sides of the calcaneus.

Figure 1:
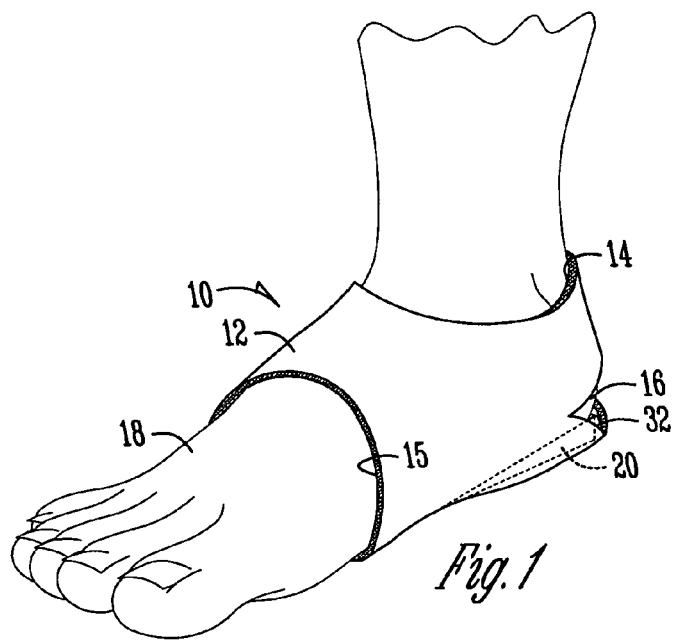
FIG. 1 is an isometric view showing one embodiment of the present invention.
Figure 2:
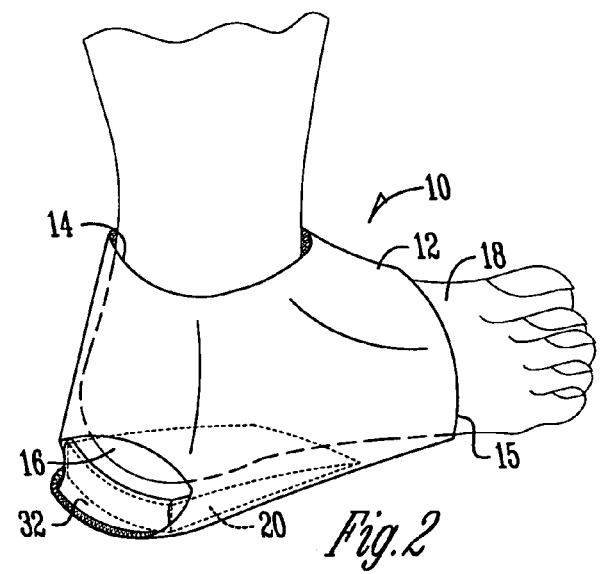
FIG. 2 is a perspective view of the embodiment shown in FIG. 1 showing the heel of the foot during use.
Figure 3:
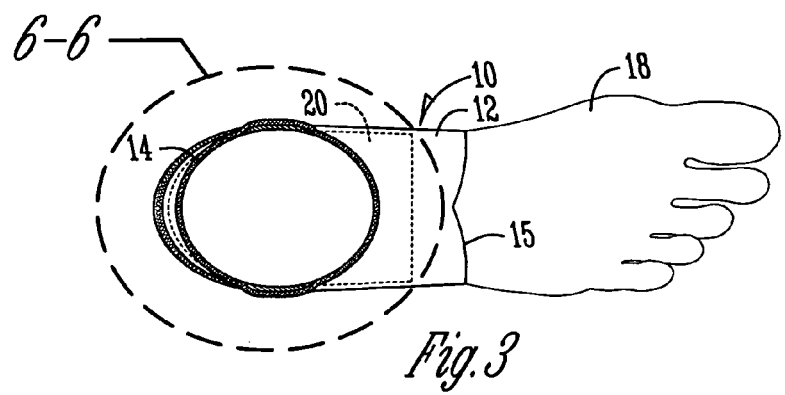
FIG. 3 is a top view of the embodiment shown in FIG. 2.
Figure 4:
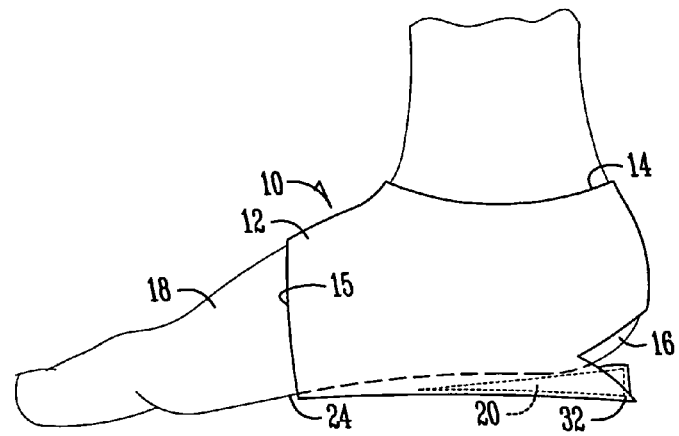
FIG. 4 is a side view of the foot from the instep side.
Figure 5:
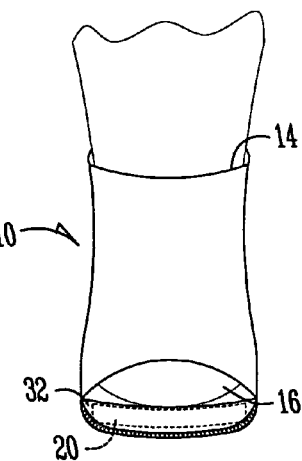
FIG. 5 is a rear view of a foot with the device.
Figure 6:
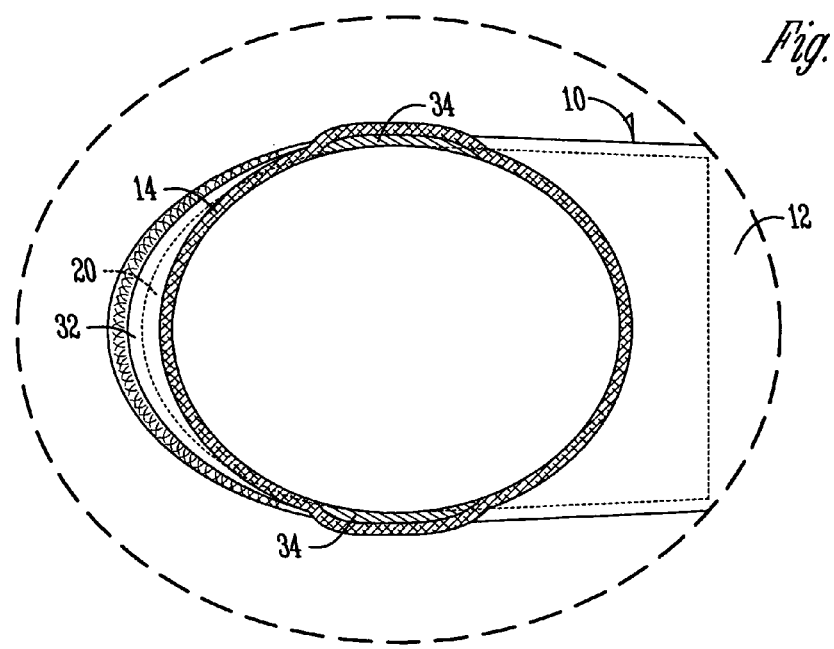
FIG. 6 is an enlarged view taken along line 6—6 in FIG. 3.

FIG. 1 shows the preferred embodiment of the present invention. The heel stabilizing device 10, is comprised of a half stocking 12 having an open top 14 and an open forward end 15. The stocking is made of a stretchable material so as to fit snugly around the posterior, lateral, medial, and plantar aspects of the heel 16 of the foot 18. Device 10 includes a pad 20 on each side of the inside surface of the stocking 12 to fit under the heel 16. The pad 20 is configured to be thickest at the part directly under the heel and get thinner as it moves forward toward the arch of the foot. As shown in FIG. 2, the pad 20 is disposed in a pocket formed by sewing a piece of material 32 to the sleeve 12. When the stocking 12 is positioned over the heel 16, it extends forward along the lateral and medial sides of the foot 18 to approximately the mid-point of the longitudinal arch 24 of the foot 18 (FIG. 2). It is important to note that the top 14 of the stocking 12 terminates at the calcaneus below the talo calcaneal joint of the foot 18 and therefore does not reach the ankle or the tibia or fibula. Together, stocking 12 and pad 20 allow absorption of heel shock.

Device 10 has mirror image left and right lateral portions, such that the device can be worn on either foot 18. The device 10 can also be used alone or in conjunction with any type of foot wear. Device 10 is also stretchable or elastic so that it may be used with different foot sizes.

Stocking 12 is preferably comprised of an elastic firm stitched material forming an elastic sleeve and is adapted to slide over the foot 18 of the user as shown in the figures to provide a tight fit around the heel 16. An example of acceptable material is neoprene. Preferably the material is cut and stitched so that the seam of it extends centrally along the bottom of the foot and up the back of the heel.

The pocket of gel material 20 is an inherently adhering plastisol material. Gel or pad 20 is a thermal gel material, adherent, soft and compliant, with a spongy feel. The gel material or pad 20 is commercially available. One suitable gel material 14 is sold by Three G Corporation of 110 West 3rd North Street, Morristown, Tenn. 37814. Such gel material need not be described with chemical particularity except to say that such materials are Plastisols and present a soft cushioning feel, even when subjected to freezing temperatures. They maintain cold temperatures when exposed to ambient 20° C. temperatures for at least 30 minutes, and in some cases, 60 minutes. Other therapeutic gel materials may be employed, for example the gel material referenced in commonly owned U.S. Pat. No. 6,267,742 relating to a night splint suspension system that can be used in combination with Sealed Ice™. Material safety data sheets are available from Three G Corporation for the Plastisol compound suitable for use in the present invention.

Stabilization of the heel 16 can be used to treat heel pain and help correct various heel-related conditions. It reduces movement and irritation to the heel which leads to inflammatory problems. This is intended to protect the heel bone from impact by absorbing some of the shock during the heel contact phase of gait. This in turn can relieve heel pain.

Pad 20 does not extend over the Achilles tendon or the posterior aspect of heel 16. Pad 20 also does not interfere with the ankles which allows the ankles to have a free range of mobility.

In the preferred embodiment pad 20 is shaped such that its thickest portion is under the rear part of the heel and it gradually descends in cross sectional thickness down to the point under the arch, 24. In this way pad 20 provides optimum cushioning for shock absorption directly under the part of the heel that carries most of the body weight. Because the sleeve or half stocking 12 is comprised of an isomeric material it provides compressive forces around the ankle which functions to treat edema and swelling with compression. And, when the pad is a cold therapy pad as it may optionally be, a combination of shock absorbing heel pad is provided, reduced inflammation with cold therapy is provided, and simultaneously treatment of edema and swelling by compression is provided. Moreover, all of this is provided in a system which fits like a stocking, feels comfortable and may be used inside of a conventional shoe without modification of most shoes. Of course, when cooling therapy is provided, the pad is cooled in a freezer up to for example two hours before wearing. Finally, for certain individuals it may optionally be used in combination with the device of U.S. Pat. No. 5,645,525.

The preferred embodiment of the present invention has been set forth in the drawings and specification, and although specific terms are employed, these are used in a generic or descriptive sense only and are not used for purposes of limitation. Changes in the form and proportion of parts as well as in the substitution of equivalents are contemplated as circumstances may suggest or render expedient without departing from the spirit and scope of the invention as further defined in the following claims.

What is claimed is:

1. A device for stabilizing the heel of a foot of a person, comprising:
    an elastic sleeve adapted to fit around the foot and heel of a person, the sleeve having a pocket, a heel opening, a front toe opening and a top ankle opening, when in operative position on a person's foot the heel opening is located at the back of the heel, the toe opening is located to position a border thereof along the longitudinal arch, the top ankle opening is located to position a border thereof to extend above the heel without making contact with the ankle so as not to affect the mobility of the ankle; and
    a pad fully enclosed within the pocket of the sleeve wherein the pocket is positioned under the heel for shock absorption in the operative position.

2. The device of claim 1 wherein the pad is a fluid-filled bladder.

3. The device of claim 2 wherein the bladder is filled with a gel.

4. The device of claim 2 wherein the bladder is filled with air.

5. The device of claim 2 wherein the bladder is filled with a liquid.

6. The device of claim 1 wherein the pad is constructed of polymeric foam material.

7. The device of claim 1 wherein the pad is a thermal gel material, adherent soft and compliant with a spongy feel which will maintain this characteristic even at cold temperatures.

8. The device of claim 1 which is used in combination with a pair of pads disposed in opposite sides of the inside of the surface of the sleeve and opposite sides of the calcaneus.

9. The device of claim 1 wherein the sleeve can be worn on either foot.

10. The device of claim 1 wherein the pad is a cold therapy pad.

11. The device of claim 1 wherein the sleeve is constructed of an elastic material stitched together at the seams to provide uniform compression about the foot and the heel.

12. The device of claim 1 wherein the pad is thickest at the portion underlying the back of the heel and gradually decrease in longitudinal cross section as it progresses forward toward the arch of the user's foot for even pressure distribution throughout the heel.

13. The device of claim 1 wherein the pocket prevents the pad from shifting about the heel for maintaining shock absorption in the operative position.

14. The device of claim 1 wherein the pocket extends substantially the width of the sleeve.

15. The device of claim 1 wherein the pocket and the pad extend across a substantial width of the sleeve for even pressure distribution throughout the heel.

* * * * *